United States Patent [19]

Wan

[11] Patent Number: 4,574,038

[45] Date of Patent: Mar. 4, 1986

[54] MICROWAVE INDUCED CATALYTIC CONVERSION OF METHANE TO ETHYLENE AND HYDROGEN

[75] Inventor: Jeffrey K. S. Wan, Kingston, Canada

[73] Assignee: Alberta Oil Sands Technology and Research Authority, Edmonton, Canada

[21] Appl. No.: 761,394

[22] Filed: Aug. 1, 1985

[51] Int. Cl.$^4$ .......................... B01J 19/12; C07C 2/00
[52] U.S. Cl. .................................. 204/162 R; 585/500
[58] Field of Search ...................... 204/162 R, 158 R; 585/500, 654

[56] References Cited

U.S. PATENT DOCUMENTS 2,859,258 11/1958 Fischer et al. ...................... 585/500
4,417,964 11/1983 Wolfram et al. ................. 204/162 R

FOREIGN PATENT DOCUMENTS 2535119 2/1976 Fed. Rep. of Germany ... 204/158 R
1234161 4/1959 France ................................ 204/162

Primary Examiner—Howard S. Williams
Attorney, Agent, or Firm—Ernest P. Johnson

[57] ABSTRACT

A process for selectively converting methane to ethylene and hydrogen is provided. Methane is brought into contact with a metal powder catalyst and subjected to a pulse train of microwave radiation for a sufficient period of time to effect conversion thereof. The reaction products are recovered.

5 Claims, No Drawings

4,574,038

MICROWAVE INDUCED CATALYTIC CONVERSION OF METHANE TO ETHYLENE AND HYDROGEN

FIELD OF THE INVENTION

The invention relates to a process for selectively converting methane to ethylene and hydrogen by the use of microwave radiation.

BACKGROUND OF THE INVENTION

Ethylene is an important primary feedstock in the petrochemical industry. In certain areas of the world, exemplary of which is Alberta, Canada, the petrochemical industry relies upon the occurrence of ethane in natural gas as its main source of ethylene. Typically, such gas would contain from two to four percent ethane content, which ethane is usually extracted at the well head and thereafter converted to ethylene. In recent years, it has been observed that the produced natural gas is becoming depleted in ethane.

Methane, thermodynamically the most stable hydrocarbon, occurs in abundance in natural gas. It would be highly desirable, therefore, to be able to effect the conversion of methane to ethylene, thereby providing an abundant source of the latter.

However, such a conversion is highly endothermic; under the high temperature reaction conditions required therefor, control of the reaction to prevent the formation of unwanted by-products is difficult.

Heretofore, the techniques tried to effect the cracking of methane have ranged from thermal techniques to low and high frequency electrode and electrodeless discharge, triboelectric discharge, plasma jets and laser irradiation.

It is generally accepted that the major products in the electric discharge decomposition of methane are $H_2$, $C_2H_6$, $C_2H_4$, and $C_2H_2$. The relative amounts of these products are usually dependent upon the experimental conditions. For example, McCarthy (R, L. McCarthy, J. Chem. Phys., 22, 1360 (1954)) reported that in a glow discharge of methane at 150–310 V/cm and at a $CH_4$ pressure of about 16 torr and residence time less than 10 s, the principal product was acetylene. Ethylene and ethane, however, were only observed as major products when the discharged methane gas was allowed to impinge directly on the wall of a cold trap at 77 K. These findings provided the evidence that free radicals, such as the $CH_3$, $CH_2$ primary radicals do not recombine instantly under such conditions but persist for some time after leaving the plasma zone.

A number of electric arc cracking of methane studies have been made by Du Pont and others giving a % conversion of methane ranging from 50 to 80. In pilot-plant experiments, Eremin (E. N. Eremin and co-workers, Zh. Fiz. Khim., 37 1487 (1963)) obtained the best conditions for the best results in the electric discharge of methane at a pressure of 40 torr and a power consumption of 3kWHr $m^{-3}$ ($10^3$ kJ liter$^{-1}$) which showed 60% of the methane was cracked and 15% $C_2H_2$ was formed.

In microwave discharge experiments, the best energy yield was reported by McCarthy; it was approximately 3600 kJ for one mole of $C_2$ hydrocarbon produced.

All of the previous methane cracking experiments have been limited to low pressure plasma/electric discharge decompositions, where the reactions presumably occurred in the gas phase. Apart from the initial cost of the high power apparatus, the energy requirements for cracking the methane under such conditions are excessive.

There is therefore a need for a simple, inexpensive process which can convert methane to ethylene in good yield.

SUMMARY OF THE INVENTION

In accordance with the present invention, there is provided a microwave-induced catalytic hydrocracking process for selectively converting methane to ethylene and hydrogen.

The process involves the utilization of a catalyst adapted to provide catalytic sites for the hydrocracking reaction and which is capable of absorbing microwave radiation. A preferred group of such catalysts is particulate metal powders comprising Fe, Ni, Co, and mixtures thereof. A more preferred catlyst comprises a mixture of Ni and Fe, most preferably 15% Fe and 85% Ni. The catalyst particles are preferably quite fine, typically being about 1 micron in size.

The catalyst is preferably pre-treated, prior to first use in the hydrocracking reaction, to clean its surface. This may be done by irradiating it with microwave radiation in the presence of $H_2$.

During hydrocracking, the microwave radiation is supplied in the form of a train of pulses. The durations of the train and the pulses are controlled to maintain the temperature at the catalyst particle surfaces at about 1400° to 1600° F., the temperature needed for the conversion to proceed with viable speed and selectivity. While it was impractical to measure the temperature being generated at the catalyst particle surfaces, a set of irradiating conditions were worked out in laboratory cell tests that just initiated surface melting of the Ni particles. The reaction was successfully carried out in accordance with those conditions.

Stated otherwise, the invention involves:
(a) the utilization of a catalyst which is operative to lower the activation energy required for the desired decomposition reaction, said catalyst having the ability to absorb microwave energy so that the temperature needed for viable decomposition is generated at the catalyst particle surfaces;
(b) the provision of energy in the reaction zone in the form of microwave radiation;
(c) and the attainment of selectivity in the production of ethylene by controlling the reaction zone temperature and limiting the duration during which the reaction zone components are subjected to the reaction conditions by pulsing of the radiation.

By the practise of the process, up to 70% conversion of methane to ethylene and hydrogen (with no observable side reactions) can be obtained with a short, low power microwave irradiation.

DESCRIPTION OF THE PREFERRED EMBODIMENT

The feedstock for the process is methane gas. Preferably it is supplied in a substantially pure and dry form.

The methane gas is conveniently introduced into the reaction zone under pressure. Typically, one may use a pressure of 0.3 to 1.0 atmospheres.

The catalyst is selected to provide catalytic sites for the decomposition reaction. More importantly, the catalyst must absorb strongly the microwave radiation in order to provide the necessary kinetic energy for the surface electrons to enhance the surface chemical reaction.

It has been found that high surface area metal powders, preferably comprising iron, nickel, cobalt, or mixtures thereof, are suitable. These materials absorb microwave radiation in the 1.5 to 3.0 GHz wavelength and are operative to catalyze the decomposition reaction. Typically, the metal powders used are 1 micron in size. Iron and nickel have been found to be particularly effective in the process. The best catalyst found to date is a 15% Fe - 85% Ni, 1 micron size powder.

Thermodynamic analysis has indicated that a catalyst particle surface temperature in the order of 1400°-1600° C. is desirable to produce ethylene in good yield with little contamination.

Testing has shown that irradiation of methane in the presence of catalyst as aforesaid in accordance with the following conditions induces some surface melting of the catalyst particles and produces ethylene in useful yield. The conditions are:

microwave source: 1.5-3.0 GHz, 80-100 watt incident power level
duration of on-time pulses: 0.5-10 seconds, preferably 5 seconds
duration of off-time rests: 20 to 60 seconds
cumulative duration of on-time pulses: 20 to 60 seconds
reaction cell internal temperature: about 50° C.

Typically, a 2.4 GHz microwave source at 100 watt incident power level, operated to provide 5 second on-time pulses for a cumulative duration of 20 seconds irradiation with off-time rests of 20-60 seconds, will produce a selective high yield of ethylene from methane in the presence of a 15% Fe - 85% Ni, 1 micron size powder catalyst.

Increased yields have been achieved by conducting a pre-treatment step on the particulate catalyst, before it is used in the reaction, to remove surface oxides. In the early stages of the development only Ni powder was used. Typically, at 1 atmosphere of methane, the first 20 to 30 seconds of microwave irradiation led only to the formation of hydrogen and soot. No ethylene was observed. After this initial period of inhibition, both ethylene and ethane were produced by continued irradiation. Typical yields were 20% for ethylene and 5% for ethane. It was suspected that the initial inhibition period was required to produce hydrogen. A series of experiments was then carried out using a gas mixture of methane and hydrogen in various compositions as the reactant. At a hydrogen composition of 20% and above, the initial inhibition period was removed. But the ethylene yield, in terms of energy consumed, was still quite low.

It was then decided to attempt to clean the catalyst surfaces. This was successfully achieved by first subjecting the catalyst to a vacuum and then irradiating the catalyst particles in the presence of hydrogen. On testing, it was found that such pre-treatment, coupled with subsequent irradiation of methane in the presence of the cleaned catalyst, would produce good yields of ethylene and hydrogen.

Without being bound by the same, it is believed that, in the present process wherein methane and selected catalyst are subjected to microwave irradiation, the catalyst fulfills two functions. First, it provides catalytic sites for the decomposition of methane, thereby lowering the energy of activation of the reaction. Secondly, the catalyst is operative to absorb the microwave irradiation. It is important to note that hydrocarbons, such as methane, do not usually have the capability of absorbing microwave radiation. Thus, in the absence of a catalyst, irradiation of methane by microwave radiation does not selectively yield ethylene and hydrogen. It is known that the surface electrons of the metal catalyst interact with the high intensity electromagnetic field generated by the microwave source, thereby transforming microwave radiation into an effective form of energy. This energy is utilized to crack or convert the methane present into ethylene and hydrogen. By controlling the overall cell reaction temperature and the catalyst surface temperature and removing the reaction products, selectivity of the reaction can be obtained.

EXAMPLE I

The following example is based on a run with a Ni-Fe (85-15%) catalyst and is presented to demonstrate the operability of the process of the invention.

The reactor cell consisted of a Pyrex TM tube having a volume of 100 ml. The cell was equipped with suitable valves connectable to fluid inlet and outlet lines. The microwave radiation was provided by a 2 GHz magnetron at about 80 watt incident power.

0.1 g of a Ni/Fe powder catalyst of 1 micron diameter was finely dispersed upon a sintered glass plate positioned in the lower section of the cell. The reaction cell was placed in the microwave cavity. The cell was then first evacuated and thereafter repressurized with hydrogen gas at about 2 atmospheres (200 kPa). The catalyst was subjected to two 5 second pulses of microwave radiation in the presence of hydrogen as a pre-treatment to remove oxide from the metal powder surface.

Pure, bottled methane was then introduced into the cell at a pressure of one atmosphere (100 kPa). The reaction cell containing methane and catalyst was then subjected to microwave irradiation from the magnetron. The irradiation was gated by a pulse controller which varied from 2 to 10 seconds on time with various durations of off-time to thereby maintain an overall cell temperature below about 50° C. The total irradiation time was 20 seconds.

The resulting gaseous mixture containing ethylene and hydrogen was passed out of the cell. Ethylene was recovered as a liquid in a cold trap, the hydrogen being recirculated. The product mixture was sampled and analyzed by gas chromatography and mass spectrophotometry.

Table I demonstrates the selectivity obtained in the reaction. The table shows the volume composition of the gas mixture after a total of 20 s microwave irradiation in a static system.

TABLE I

|  | Before | After Experimental | Calculated (theoretical)** |
|---|---|---|---|
| Methane | 100% | 21.8 | 22% |
| Ethylene | 0% | 51.3% | 52% |
| Hydrogen | 0% | 26.7% | 26% |

**the calculated yields were based upon the conversion: $2CH_4 = C_2H_4 + 2H_2$

EXAMPLE II

This example illustrates the operability of the process using Ni and Co alone as the catalysts.

The runs of this example were in all respects the same as those of Example I, except that the catalysts in separate runs were Ni and Co respectively.

With Ni as the catalyst, the maximum % conversion of methane to ethylene gave 16.0% of ethylene. Traces of ethane were also detected.

With Co as the catalyst, the maximum % conversion of methane to ethylene gave 14.6% of ethylene.

The embodiments of the invention in which an exclusive property or privilege is claimed are defined as follows:

1. A process for converting methane to ethylene and hydrogen comprising:
   providing methane in a reaction zone containing a catalyst, said catalyst being capable of absorbing microwave radiation;
   irradiating the methane in the presence of said catalyst with pulsed microwave radiation for a sufficient period of time, to thereby convert methane to ethylene and hydrogen; and
   recovering said reaction products.

2. A process as set forth in claim 1 wherein:
   the catalyst is a metal powder comprising Ni, Co, Fe, and mixtures thereof.

3. A process for converting methane to ethylene and hydrogen comprising:
   providing a metal powder catalyst, comprising Ni, Co, Fe, and mixtures thereof, in a reaction zone;
   activating the catalyst by removing surface oxides therefrom;
   introducing methane into the reaction zone;
   irradiating the methane in the presence of the catalyst with pulsed microwave radiation, the duration and number of said pulses being controlled to convert the greatest part of the methane to ethylene and hydrogen; and
   recovering said reaction products.

4. The process as set forth in claim 3 wherein:
   the microwave radiation wavelength is in the range of about 1.5 to 3 $GH_z$.

5. The process as set forth in claim 4 wherein:
   the microwave radiation is supplied in pulses of about 0.5 to 10 seconds with off times of about 20 to 60 seconds, the cumulative duration of the pulses being about 20 to 60 seconds.

* * * * *